United States Patent [19]

Krüger

[11] Patent Number: 5,454,364
[45] Date of Patent: Oct. 3, 1995

[54] INSERTION ASSISTING DEVICE FOR MEDICAL INSTRUMENT

[76] Inventor: Peter C. Krüger, Curtiustrasse 4, 2400 Lübeck, Germany

[21] Appl. No.: 979,945

[22] Filed: Nov. 23, 1992

[30] Foreign Application Priority Data

Nov. 21, 1991 [DE] Germany .................. 41 38 240.4

[51] Int. Cl.⁶ ..................................... A61B 1/00
[52] U.S. Cl. ................ 600/114; 604/95; 600/116
[58] Field of Search ............... 128/4, 6; 604/95, 604/96, 97

[56] References Cited

U.S. PATENT DOCUMENTS

| | | | |
|---|---|---|---|
| 2,767,705 | 10/1956 | Moore | 128/4 |
| 3,485,237 | 12/1969 | Bedford | 604/95 X |
| 3,895,637 | 7/1975 | Choy . | |
| 4,066,070 | 1/1978 | Utsugi | 128/4 |
| 4,148,307 | 4/1979 | Utsugi | 128/4 |
| 4,207,872 | 6/1980 | Meiri et al. | 128/4 |
| 4,321,915 | 3/1982 | Leighton et al. | 128/4 |
| 4,447,227 | 5/1984 | Kotsanis . | |
| 4,561,427 | 12/1985 | Takada | 128/4 |
| 4,577,621 | 3/1986 | Patel | 128/4 |
| 4,676,228 | 6/1987 | Krasner et al. | 128/4 |
| 4,690,131 | 9/1987 | Lyddy et al. . | |

FOREIGN PATENT DOCUMENTS

| | | | |
|---|---|---|---|
| 2481915 | 11/1981 | France | 128/4 |
| 1170586 | 5/1964 | Germany . | |
| 3630660 | 3/1988 | Germany | 128/4 |
| 1216238 | 8/1989 | Japan | 128/4 |
| 1216240 | 8/1989 | Japan | 128/4 |

Primary Examiner—Richard J. Apley
Assistant Examiner—Beverly A. Meindl
Attorney, Agent, or Firm—Panitch Schwarze Jacobs & Nadel

[57] ABSTRACT

A medical instrument, particularly an endoscope, is provided with a device to guide the instrument within the intestine. The device is forwardly movable stepwise within the intestine with intermittent contact with the intestine wall. The device is so constructed to enable one to first push together on the instrument a part of the intestine surrounding the instrument, and then the device can be quickly pushed forward by taking advantage of the intestine's own inertia.

13 Claims, 2 Drawing Sheets

INSERTION ASSISTING DEVICE FOR MEDICAL INSTRUMENT

FIELD OF THE INVENTION

The invention concerns a medical instrument, specifically an endoscope, with a device for guiding within the intestine, which may be moved forwardly stepwise, with intermittent engagements with the intestine wall.

BACKGROUND OF THE INVENTION

The guiding of medical instruments, particularly endoscopes, within the intestine, frequently entails problems. Using instruments without a specific device to guide them, the forward movement can only be accomplished by applying pressure from outside the body, either directly on the instrument itself or, indirectly through pressure on the corresponding part of the body. Due to the many turns of the intestine, such guidance, without an accessory device, can be problematic, time consuming and frequently painful for the patient; particularly when it is necessary to enter into further inwardly located sections of the intestine. Finally, there is the risk of perforation or other forms of injury of the intestine by moving the instrument forward.

It is known to insert such a medical instrument stepwise with intermittent engagements with the intestine wall. For this there is provided at the distal end of the instrument an accessory device which consists of at least two parts, which may lie against the intestine wall for purpose of support, and which are movable toward each other along the axial direction of the instrument. In this manner a forward movement of the instrument within the body at the distal end of the instrument is accomplished, so that the following part of the instrument is practically pulled into the intestine. Such a device is known from DE 36 31 352 A1.

Such accessory devices for the guidance of these instruments within the intestine generally serve their purpose. However, in practice they also have disadvantages. For this caterpillar-like known movement within the intestine is time consuming and entails a latent risk of injuring the intestine wall. Such guiding devices are also technically complex and thus susceptible to damage. Finally, there are frequently design-related problems in the cleaning and disinfection process, since these devices cannot, for cost reasons, be produced as disposable items. This is of particular importance due to the increasing problem of AIDS.

From this background, the object of the invention is to create a medical instrument of this type, with a device for the guidance within the intestine, which allows a smooth and safe guiding within the intestine with almost complete avoidance of the previously mentioned disadvantages.

SUMMARY OF THE INVENTION

According to the invention, this object is achieved by constructing such an instrument with guidance device in such a manner that a section of intestine wall surrounding the instrument can by means of the device be pushed together on the instrument and that the device then, by taking advantage of the intestine's inertia, can be quickly moved forward. The wall of the intestine is, so to speak, pulled onto the instrument, which after several such cycles is manually led in. By this means a very quick and simultaneously risk-free and pain-free passing of the instrument through the intestine is possible. The forces applied to the intestine wall are minimal. The contraction and with it the pushing up of the intestine wall on the instrument are achieved in a defined manner, whereby the risk of injury is minimized.

Preferably, there is only one chamber provided for application to the intestine wall and this is contractable and expandable by pressure control. By means of this chamber the instrument is intermittently brought against the wall of the intestine, which is then together with the chamber contracted in the axial direction of the instrument. Thereafter follows a depressurization, whereby the chamber expands in the axial direction of the instrument and thus travels further into the inside of the intestine toward the small intestine.

The device is preferably placed at the distal end of the instrument (e.g., endoscope), whereby the proximal end of this device is rigidly mounted on the instrument and the distal end is slideably mounted.

In order to guide the instrument, the device in particular, against the intestine wall, it can either be expanded in the (radial) direction toward the wall of the intestine, or the intestine wall itself can be pulled toward the device. For the first mentioned solution, for example, a ringshaped collar can be provided which by means of radial expansion through pressure increase places itself against the intestine wall. There will preferably be provided several flexible collars which are communicating with each other and interconnected and which, towards their axial direction of contraction, are spring and/or pressure controlled; that is, independently expandable. At the same time these collars are arranged in a manner in which with the radial expansion an axial contraction is simultaneously achieved, whereby the intestine during the radial expansion of the collar is essentially pushed together around the instrument. The collars are moveably mounted on the instrument.

The contraction in the radial direction occurs through collapse of the flexible collars; yet an additional force is necessary in the axial direction which, for example, could be created by an elastic tube, serving as a spring-return mechanism which is firmly attached at one end to distal ends of the collars and at the other end to the distal end of the instrument. To keep the intestine from moving back simultaneously with the collars during the spring-back in the axial direction, but on the contrary, to keep it pushed up onto the instrument, it is necessary that the collars are first relieved from pressure and then, after being separated from the intestine wall, are moved distally. For that purpose, a locking-device is provided which fixes the collar in an axial position at least until the separation from the intestine wall has taken place. Not until then does a forward movement of the collars take place by taking advantage of the self-inertia of the intestine, which stays in its pushed up position around the instrument. Such a locking device can, for example, be formed by a ring, in connection with one of these controlling pressure-tubes, so that the tube during pressure increase expands radially and thereby the ring gets locked onto the instrument. During pressure relief the ring can slide on the instrument.

In a preferred embodiment a spring-actuated tube is arranged on the interior of the chamber. Around its circumference the tube has small openings toward the chamber whereby the pressure effective area of these openings is smaller than the area at the distal end of the tube. The locking of the distal end of the tube can be pressure controlled and through the tube, the pressure increase can be conveyed. For this purpose, an elastic tube is provided on the distal side of the collar, which encloses the spring-actuated tube toward the instrument, and which, in case of a sudden pressure decrease, instantly deflates and thus fixes the distal end of the collar onto the instrument. Since the pressure effective area of the tube openings leading toward the chamber is smaller than the pressure effective distal front surface at the end of the tube, a repeated pressure increase first unlocks the locking device, so that the collars expand distally, and during further pressure increase a radial expansion to a position on the intestine wall is achieved.

Instead of positive pressure, a corresponding negative pressure can also be used to bring the device in touch with the wall of the intestine. For this purpose circumferential openings are provided over the entire length of the device in order to suck in the wall of the intestine. Such a chamber with openings can for example be formed of a pleated bellows or a spring tube where the openings are possibly positioned at a deep point, that is, on the side nearest the instrument, so that the intestine wall lies uniformly around the chamber and a point of concentrated pressure impact against the intestine wall is avoided.

Using a pleated bellows, the contraction takes place by applying negative pressure. This can be increased by a flexible, non-extensible tube that is pulled over the pleated bellows, which in order to compensate for in-chamber pressure levels must have suction openings as well.

BRIEF DESCRIPTION OF THE DRAWINGS

The invention is further explained by means of the embodiments illustrated in the drawings. These are shown in a very schematic and simplified form as follows.

DETAILED DESCRIPTION OF PREFERRED EMBODIMENTS

Figure 1:
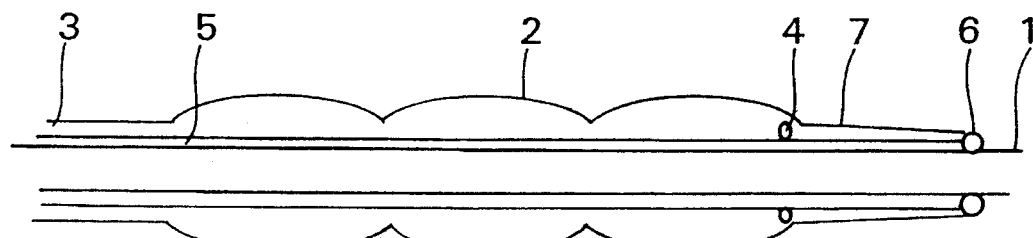
FIG. 1 shows a distal part of the instrument with a mounted device for guiding in the intestine.

In the figures reference numeral 1 represents the distal end region of a medical instrument, an endoscope for example. On this instrument is mounted a guiding device, which is fixed on the proximal side of the instrument (in the figures on the left side) and on the distal side is slideably held on the instrument.

Figure 2:
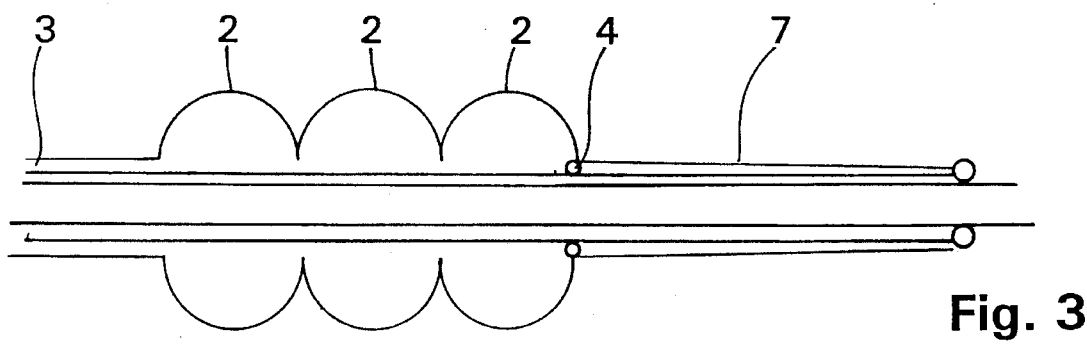
FIG. 2 shows the device according to FIG. 1 but in a different working position.
Figure 3:
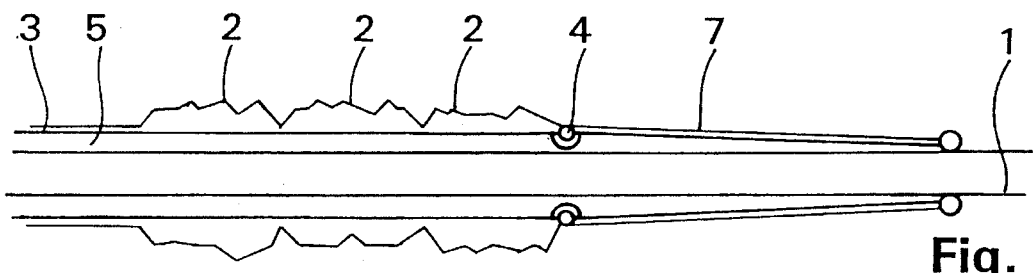
FIG. 3 shows the device according to FIG. 1 in a third working position.

The devices depicted in FIGS. 1–3 consist of three flexible, non-stretchable collars 2, arranged one after the other on the instrument 1. The collars are interconnected and intercommunicating, and their pressure is controllable by means of a pressure line 3. The pressure line 3 is connected with the proximal end of the instrument 1. The collars 2 are connected at the distal end with a ring 4, which is part of a locking device. The ring 4 does not rest directly on the instrument 1, but is separated from the instrument 1 by a pressure line 5 which surrounds the instrument 1 in this region and which is also part of the locking device. Upon an increase of pressure in the line 5 the ring 4 becomes axially fixed on the instrument and thus locked. Whereas upon a reduction of pressure the ring 4 becomes mobile.

The guiding device is, at its distal end, closed by a ring 6, which is fixedly mounted on the instrument 1. Between this ring 6 and ring 4 an elastic tube 7 is placed which serves as a driving spring element.

The operation of the guiding device depicted in FIGS. 1–3 is as follows:

In the complete relief position depicted in FIG. 1, in which the lines 3 and 5 are pressure relieved and the tube 7 is relaxed, the instrument 1 is at this point inserted a little ways into the intestine. After this the pressure in line 3 is increased whereby the collars expand radially. At this point the collars lie against the wall of the intestine (not shown) and thus carry it with them during their following contraction in the axial direction of the instrument so that a section of the intestine is caused to slide onto the instrument 1. The device then assumes the position depicted in FIG. 2. Next, the pressure is increased in line 5 whereby ring 4 becomes fixed onto instrument 1. It is not until the ring 4 is locked in place that the collars 2 are pressure relieved through line 3 at which point they radially collapse and become separated from the pushed-together intestine wall. The position depicted in FIG. 3 is thus reached. Thereafter, pressure is relieved in line 5, whereby the locking of the ring 4 becomes pushed up, and due to the tension of the elastic tube 7, the ring 4 together with the attached collar is pulled distally back to the position depicted in FIG. 1. A section of the intestine at this point lies pulled up around the instrument. After several such work cycles it is then possible to insert the instrument considerably further.

Figure 4:
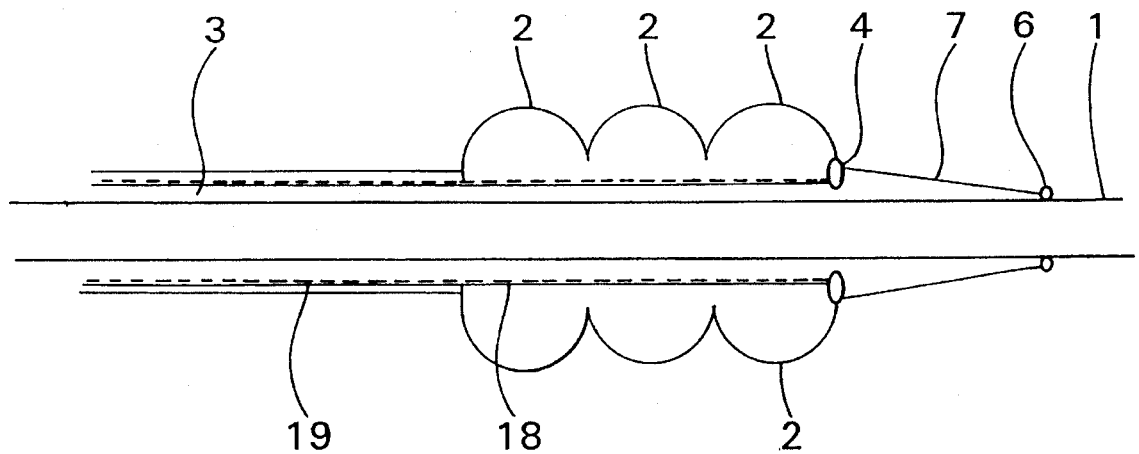
FIG. 4 shows a further embodiment of the device according to FIG. 1, functioning with collars.

In the embodiment of FIG. 4 the pressure is supplied exclusively through line 3. The collars 2 are positioned on an axial spring elastic tube 19 which surrounds the instrument and which is connected with the collars 2 and communicates therewith through openings 18. The pressure increase in the collars 2 evolves in the same way as previously described in connection with FIGS. 1 and 2. Then, once the intestine is pushed onto the instrument 1 through the axial contractions, the contact of the collars 2 with the intestine wall is interrupted by a sudden release of pressure through line 3. Not only do the collars 2 collapse due to the sudden pressure release, but also the elastic tube 7 between the rings 4 and 6, whereby the ring 4 is cohesively fixed on the instrument 1. After the collars have collapsed far enough, the pressure in tube 3 is again increased. Due to the fact that the pressure effective area of the openings 18 is smaller than the pressure effective surface at the distal end of the tube, which is formed by a part of the ring 4 and by the tube 7, the result of a repeated pressure increase is a distalward movement of the ring 4 and then a radial expansion of the collars 2.

The devices shown in FIGS. 5 through 9 function with negative pressure, that is, the intestine wall is pulled against the instrument by means of negative pressure and then shoved together on it, whereafter by taking advantage of the intestine's own inertia after a short pressure increase, it is quickly pushed forward.

Figure 5:
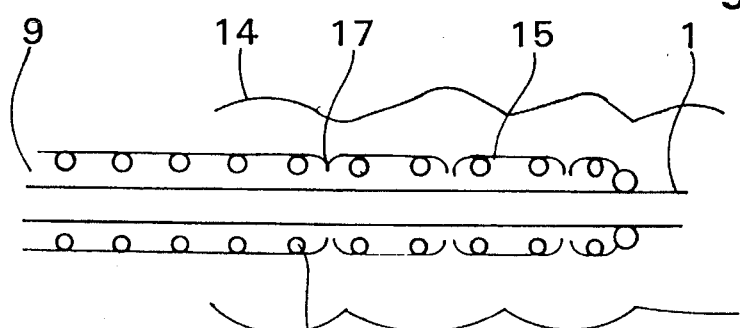
FIG. 5 shows a device according to FIG. 1, functioning with a spring tube.
Figure 6:
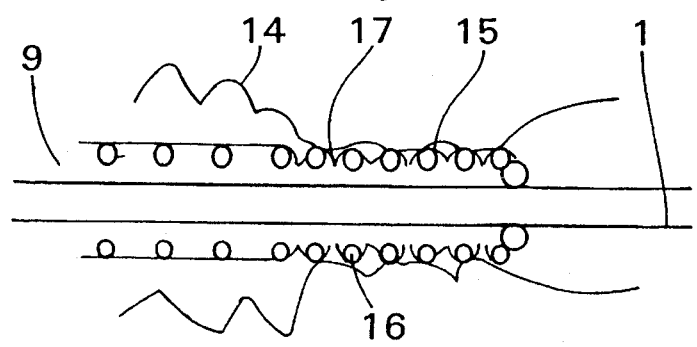
FIG. 6 shows the device according to FIG. 5 in a second working position.

In a further embodiment according to FIGS. 5 and 6, a section of the intestine is designated 14. The device here consists of a flexible tube 15, which is proximally fixed and distally slideably mounted on the instrument and which by means of a helically coiled spring 16 arranged in the distal direction is thereby supported in the axial expansion direction in the manner of an expansion spring. The tube 15 is connected to a pressure line 9 and has openings 17 through which the intestine wall 14 is sucked onto as well as again separated from it.

The operation of this device is clearly recognizable through FIGS. 5 and 6. In the first working step a negative pressure is created in the tube 15, so that the surrounding intestine wall is sucked onto the periphery of the tube 15 and finally, as soon as a sealed system has been created between the tube and the intestine wall, the tube 15 at its end region in the axial direction of the instrument contracts due to the negative pressure. The openings 17 of this embodiment are positioned as far inward as possible in order to prevent an injury to the intestine wall by a pressure increase.

When the tube 15 has finally reached its completely contracted position, it is impacted with an increased pressure, so that the pushed up section 14 of the intestine is lifted off the tube 15 and the tube 15 by means of the force of the helical spring 16 is moved forward toward the distal end of the instrument. Then a new cycle begins.

Figure 7:
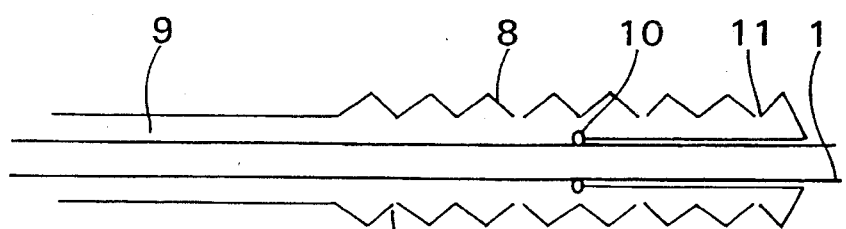
FIG. 7 shows a device according to FIG. 1, functioning by means of a pleated bellows.

FIG. 7 depicts an instrument 1 with a pleated bellows 8 which by means of a line 9 leading to the proximal end of the instrument, is actuated with either positive or negative pressure. The pleated bellows 8 is fixedly mounted to the instrument at its proximal end and at its distal end is slideably arranged on the instrument 1. It is sealed against the instrument by means of a seal 10 which is fixed to the instrument. This device works in the same way as previously described for the device of FIGS. 5 and 6.

Figure 8:
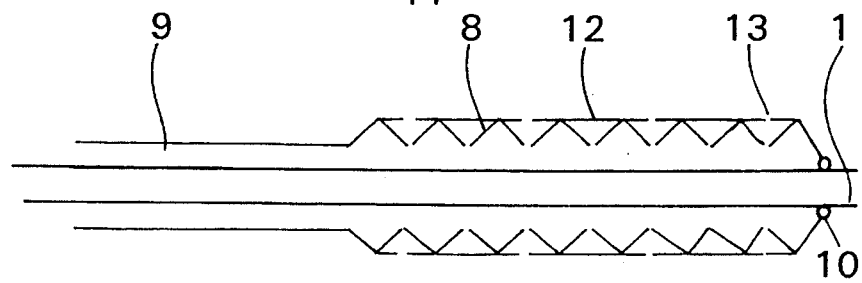
FIG. 8 shows another embodiment of a device according to FIG. 1, functioning by means of a pleated bellows.

The embodiment of FIG. 8 differs from FIG. 7 first in the arrangement of the seal 10 and second in its having an outer sheath 12. The seal 10 is positioned in this embodiment at the distal end of the pleated bellows and slides on the instrument. The sheath 12 surrounds the pleated bellows 8 completely and has openings 13 through which the evolving pressure level in line 9 is further conducted. The sheath 12 causes a power increase during the contraction of the pleated bellows 8. Because of the smoother outer surface, it is possible to achieve a more protective pushing on of the intestine as well as an easy rectal insertion.

In the described embodiments according to FIGS. 5 through 9 the openings 11 or 17 can be so designed that they take on a certain valve function, that is they preferably allow a stream from the outside toward the inside and are reduced in area in the opposite direction.

Figure 9:
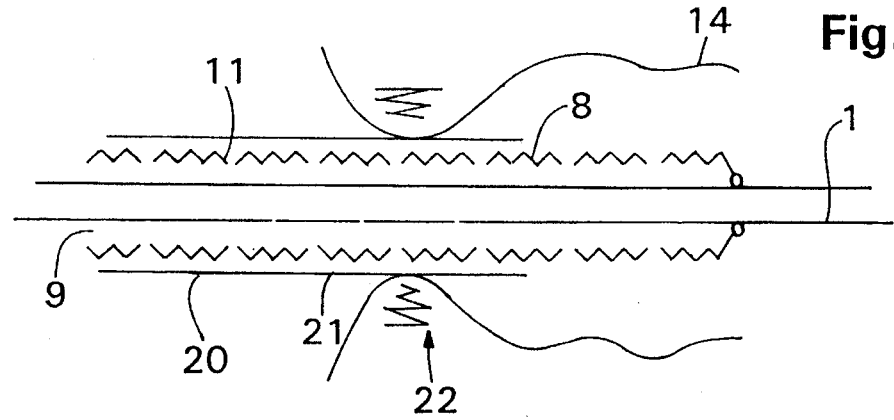
FIG. 9 shows a device according to FIG. 1 during rectal insertion.

In FIG. 9 an instrument 1 is depicted with a guiding device as has been described for example with reference to FIGS. 5 through 8, that is a device with which the intestine wall 14 is contacted by using negative pressure. With these devices, which have intake openings distributed all along their length and around their periphery, it is necessary for rectal insertions to assure that the part of the device which has not yet been inserted into the intestine is sealed against the outside, in order for the necessary negative pressure to build up in the section of the instrument which is located inside the intestine. For that purpose a foil sleeve 20 is provided, which provides insertion assistance in the form of a pipe 21 and extends to the proximal end of the device and which seals this region from the outside. The pipe 21 is inserted in the area of the adductor muscle 23 to avoid radial load and injury to the intestine.

It will be appreciated by those skilled in the art that other changes could be made to the embodiments described above without departing from the broad inventive concept thereof. It should be understood, therefore, that this invention is not limited to the particular embodiments disclosed, but it is intended to cover all modifications which are within the spirit and scope of the invention, as defined by the appended claims.

I claim:

1. A medical instrument comprising an endoscope having a longitudinal axis and a device for guiding the endoscope within an intestine, said instrument being forwardly moveable stepwise by intermittent contact of the device with an intestine wall, said device comprising a single chamber with proximal and distal ends for engaging a portion of the intestine wall surrounding said instrument and pressure actuation means for contracting and expanding the chamber in the axial direction of the endoscope, whereby upon changes in pressure of the pressure actuation means the device alternately pushes a portion of the intestine wall together and can be quickly pushed forward in the intestine by taking advantage of the intestine's own inertia.

2. A medical instrument according to claim 1 wherein the chamber is fixedly connected at its proximal end with the endoscope and at its distal end is slidably held on the endoscope.

3. A medical instrument according to claim 1 wherein the chamber is held on the endoscope by means of an elastic tube.

4. A medical instrument according to claim 1 wherein the chamber comprises a plurality of flexible collars connected to and in pressure communication with each other, said collars being actuated in the distal direction along the longitudinal axis of the endoscope by spring or pressure force.

5. A medical instrument according to claim 4 wherein the collars are connected at their distal end with an axial elastic tube which is attached to the distal end of the endoscope, and wherein the distal end of the collars is fixable on the endoscope by means of a locking device.

6. A medical instrument according to claim 5 wherein the locking device comprises a ring which, when actuated by a pressure increase, is fixed to the instrument.

7. A medical instrument according to claim 1 wherein the chamber has an inside surface which is mounted on a spring force-actuated tube, said tube having a distal end and being provided around its periphery with openings leading to the chamber, wherein the pressure effective area of the openings is smaller than the pressure effective surface at the distal end of the tube.

8. A medical instrument according to claim 1 wherein the chamber has a region which will contact the intestine wall and is provided with openings along the entire length of said region, said openings functioning to suck the intestine wall thereagainst.

9. A medical instrument according to claim 1 wherein the chamber comprises an elastic pleated bellows.

10. A medical instrument according to claim 9 wherein the pleated bellows is provided with openings near an inner diameter of the bellows.

11. A medical instrument according to claim 9 wherein the pleated bellows is enclosed in an elastic sheath which is provided with openings for sucking the intestine wall thereagainst.

12. A medical instrument according to claim 1 wherein the chamber is in the form of a spring tube which comprises a helically coiled spring extending the length of the tube, whereby the force of the spring is directed in the distal direction of the chamber.

13. A medical instrument according to claim 1 further comprising means for assisting insertion, said means having proximal and distal ends and comprising a supporting body surrounding the instrument, and said means further comprising a flexible tubular seal which closes off the proximal end of the insertion assist means.

* * * * *